United States Patent [19]

Fenton

[11] 4,423,238

[45] Dec. 27, 1983

[54] PROCESS FOR PURIFYING ACETALS

[75] Inventor: Jeff T. Fenton, Ponca City, Okla.

[73] Assignee: Conoco Inc., Ponca City, Okla.

[21] Appl. No.: 378,660

[22] Filed: Jun. 17, 1982

[51] Int. Cl.$^3$ ................. C07D 323/06; C07D 321/06; C07D 323/00; C07D 319/06; C07D 317/12; C07D 41/58
[52] U.S. Cl. .................................... 549/368; 549/353; 549/369; 549/430; 549/352; 549/347; 568/672
[58] Field of Search ............... 549/368, 353, 369, 430, 549/352, 347; 568/672

[56] References Cited

U.S. PATENT DOCUMENTS 3,580,928 5/1971 McAndrew et al. ............... 549/368
3,607,882 9/1971 Wenger ............................... 549/368
3,985,770 10/1976 Collman et al. .................... 423/418
4,026,873 5/1977 Iguchi et al. ....................... 549/368

*Primary Examiner*—Norma S. Milestone
*Attorney, Agent, or Firm*—Cortlan R. Schupbach, Jr.

[57] ABSTRACT

A method of purifying trioxane and other acetals by contacting them with an alkali metal and a phase transfer catalyst is described. Trioxane so purified is capable of being polymerized to high molecular weight.

7 Claims, No Drawings

PROCESS FOR PURIFYING ACETALS

This invention relates to a process for the purification of acetals. More specifically, this invention relates to a process for removing impurities such as water, formic acid, methyl formate and methylal from trioxane by reacting the impurities with an alkali metal in the presence of a phase transfer catalyst.

Trioxane, which is the cyclic trimer of formaldehyde, is normally manufactured by heating aqueous formaldehyde solutions in the presence of a strong mineral acid such as sulfuric or hydrochloric acids. Unfortunately, the trioxane recovered from such a process contains impurities. These impurities include water, formic acid, methanol, methylal, and methylformate. When trioxane containing these impurities is polymerized, most of the impurities act as chain transfer agents, thereby causing the resulting polymer product to have a lower molecular weight than otherwise possible when these impurities are absent. The molecular weight of the oxymethylene polymer decreases as the amount of these impurities contained in the monomer feed increases. Impurities in trioxane can reach concentrations such that polymerization is severely retarded.

The impurities removed by the process of the present invention include water and aldehydes upon which acetals are based, alcohols, and addition products of the same which result from the manufacture. These impurities interfere with the cationic polymerization of the acetal and are normally inherent in acetals because of the method by which they are formed.

The major use for these acetals is in polymerization reactions and the presence of a small amount, i.e. 100 parts per million, of such impurities in the monomer feed would cause sufficient chain transfer reactions to occur such that the resulting molecular weight is not sufficiently high to provide a useful polymer.

Initially, attempts were made to purify the acetals by distillation and recrystallization. However, such purification schemes do not sufficiently reduce the amount of impurities contained in the acetals to provide improved polymerization reactions unless such polymerizations and recrystallizations are carried out under stringent conditions and comprising many steps, all of which make such a process economically prohibitive on a commercial basis.

Many attempts have been made in the art to improve the process for purifying acetals. U.S. Pat. No. 4,026,873 refers to polyoxymethylene crystals prepared from trioxane wherein prior to polymerization the trioxane is purified by refluxing in the presence of sodium wire. U.S. Pat. No. 3,580,928 relates to a process for purifying acetals where the acetal is purified by contacting with liquid sodium, allowing a precipitate to form and removing the precipitate from the solution. U.S. Pat. No. 3,607,882 deals with a method of removing impurities of trioxane and other acetals by forming an alkali metal ketyl which remains as a bottom under separation via distillation to provide a purified acetal. However, this method is not suitable since large quantities of ketones are required and large amounts of residue remain unless great care is taken. In addition, it has been found that attempts to use this procedure result in unpredictable quality during the removal of the impurities.

It would therefore be of great benefit to provide an improved method wherein a rapid, economical removal of impurities from acetals such as trioxane could be carried out.

It is therefore an object of the present invention to provide an improved process for the removal of impurities from acetal such as trioxane. Other objects will be apparent to those skilled in the art as the description proceeds.

In accordance with the present invention acetals containing impurities such as water, alcohols and aldehydes, or mixtures of these are purified by reacting the impurities with an alkali metal in the presence of a phase transfer catalyst and thereafter recovering from the residual reaction products a purified acetal containing substantially no impurities.

In the prior art the use of an alkali metal such as described in U.S. Pat. No. 4,026,873 satisfactorily removed impurities from the acetals. However, such a reaction requires vigorous and lengthy refluxing. Since the alkali metal is in a completely different physical state than the impurities, lengthy reaction times and severe conditions are required in order to remove substantially all impurities. This difficulty is solved by the process of the present invention, which utilizes in addition to the alkali metal a phase transfer catalyst in order to make the reaction more efficient, proceed to completion more quickly and provide low levels of residue after well known separation techniques such as fractionation.

Thus the present invention provides a method for removing impurities from trioxane, cyclic acetals and linear acetals.

Acetals which can be purified using the process of the present invention are those having the general structure

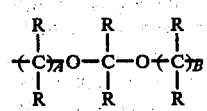

wherein A and B are numbers from about 1 to about 3, R is hydrogen or a hydrocarbon radial having from 1 to about 20 carbon atoms, cyclic aliphatic or aromatic radicals having from 6 to about 20 carbon atoms, or mixtures of these. The present invention comprises contacting said trioxane or acetal or mixtures of these with an alkali metal in the presence of a phase transfer catalyst, refluxing for a time sufficient to react with impurities present, and removing the alkali metal and phase transfer catalyst.

Representative examples of acetals which may be purified using the method of the present invention are trioxane, tetraoxane, 1,3-dioxane, 4-methyl, 1,3-dioxane, 1,3-dioxolane, 1,3,6-trioxacyclooctane, 1,4-butane-diolformal, 1,4-butenediolformal, methoxymethylal, methylal and dimethoxymethylal. The present invention is especially effective with trioxane, which is polymerizable in and of itself or can be copolymerized with other monomeric compounds to form polyoxymethylene polymers and copolymers.

The acetals treated using the method of the present invention can contain high amounts of impurities, i.e. 5 weight percent or more based upon the weight of the acetal. Normally, as produced, such acetals will contain from about 0.05 to about 5.0 weight percent of such impurities. Normally, water and methanol are the predominant impurities.

The alkali metals useful in the present invention include sodium, potassium, lithium alloys and mixtures of these, and of these, sodium and potassium are more preferred with sodium being the most preferred metal. Mixtures of metals may also be used. For example, sodium-potassium alloys.

The amount of alkali metal present in the reaction during purification will depend, of course, upon the level of impurities present in the acetal to be purified together with the type of phase transfer catalyst being employed in order to accelerate the reaction. Normally, however, the amount of alkali metal present will range from about 0.1% by weight to about 10% by weight based upon the weight of the acetal. The present invention utilizes a 1:1 reaction between the active, impurity removing sodium specie ($Na^{-1}$) and the impurity itself. Thus, at least about a 2:1 mole ratio of Na:impurity is necessary, since the reaction is believed to proceed:

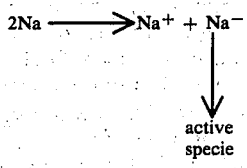

although his mechanism is theoretical and I do not wish to be bound thereby.

Phase transfer catalysts useful in the process of the present invention are those which are effective in promoting the reaction between the impurities and the alkali metal and specifically, those PTC's which cause alkali metals solubilization in organic phases. Phase transfer catalysts are effective when, in a system of two phases, the phase transfer agent and catalytic quantities brings one reactant from its normal phase into the phase of the second reactant such that reaction between the two can occur with reasonable speed. In principal the transfer of species may be any chemical agent, but normally organic phases will be used. Thus the phase transfer catalyst useful in the present invention are crown ethers and polyethylene glycol.

The phase transfer catalysts are normally present at concentrations of from about 0.01% by weight to about 10 weight percent based upon the weight of trioxane or acetals present.

Crown ether phase transfer catalysts are useful in the practice of the present invention (together with cryptates) as are polyether phase transfer catalysts.

Both macrocyclic (crown ether) materials and macrobicyclic (cryptate materials) are useful in the practice of the present invention. These materials are normally extremely complex and have no encompassing general formulas. However, representative but non-exhaustive examples of crown ethers useful in the practice of the present invention include 15-crown-5-ether, 18-crown-6-ether, dibenzo-18-crown-6 ether, dicyclohexyl-18-crown-6-ether, benzo-15-crown-5-ether, alkyl-18-crown-6-ether, alkyl-2,2,2-cryptate ether, benzo-2,2,2-cryptate, 2,2,2-cryptate, 2,2,1-cryptate, 2,1,1-cryptate, dibenzo-24-crown-6, and 12-crown-4.

Crown ethers are chosen depending on the alkali metal used. That is, 12-crown-4 is best for Li, 15-crown-5 for Na, and 18-crown-6 for K. Mixtures of metals would require, optimally, a mixture of crowns. Cryptates and polyethers are less specific since they contain flexible linkages allowing these materials to "wrap" around the metal ion.

In addition, analogues of crown ethers containing silicon, nitrogen or sulfur and analogues of cryptates containing nitrogen or sulfur are also useful in the practice of the present invention as they have donor properties similar to the crown ethers containing only carbon oxygen in the linkages. Representative examples of structures of such analogues are described.

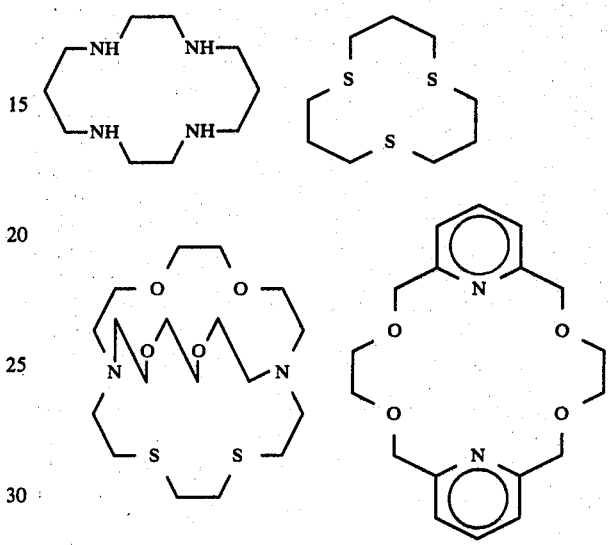

Polyethers of the general formula

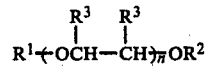

where $R^1$, $R^2$ are, independently, hydrogen atoms or alkyl radicals containing from 1 to 20 carbon atoms and $n \geq 1$.

Representative but non-exhaustive examples of polyethers useful in the present invention are polyethylene glycol of varying molecular weight of the formula $HO-(CH_2CH_2O)_nH$ where n is from 1 to 14, glyme, diglyme, propylene glycol methyl ether, diethylene glycol methyl ether, diethylene glycol n-butylether. Mixtures of these catalysts can be used.

Normally, the impurities are converted to alkali salts which ar normally solids and can be separated from the acetal by sedimentation, filtration, distillation and the like. However, depending upon the phase transfer catalyst used, normally distillation or fractionation is the preferred method since this will allow the crown ethers, as catalysts to remain in the system with unused alkali metal from the reaction mixture for reuse. However, the process of the present invention requires only one distillation to be totally effective in removing sufficient impurities to allow polymerization to proceed to high levels.

The method of the present invention is carried out at a temperature sufficiently high to allow reaction to proceed with a reasonable rate of speed, and will vary with the boiling point of the acetals undergoing purification. Normally temperatures of from about 40° C. to about 200° C. are used and preferably from about 65 to about 120° C. are preferred.

In general, the mixture of acetal, alkali metal and phase transfer catalyst will be allowed to reflux for a time and at a temperature to react all impurities.

The method of the present invention is normally carried out at atmospheric pressure. However, if reaction system pressure is increased, temperatures are normally lower so as to avoid decomposition of the acetal. However, pressure or lack of pressure is not detrimental to the present invention and thus higher or lower pressures than atmospheric may be used. It is simply more convenient to carry out the instant invention at atmospheric pressure.

Normally the reaction system is carried out in the presence of an inert medium such as nitrogen, argon, or any inert gas with respect to the system in order to restrict introduction of water into the reaction systems.

Normally, the method of the present invention is carried out for a time ranging from about 1 minute to about 10 hours and preferably from about 10 minutes to about 5 hours with reaction times of from about 2 to 4 hours being most preferred.

The instant invention is more concretely described with reference to the examples below wherein all parts and percentages are by weight unless otherwise specified. The examples are intended to illustrate the present invention and not to limit it.

EXAMPLE 1

Commercial trioxane, 225 g, was placed in a 3-neck flask which was flushed with argon. The flask was heated to melt the trioxane. Freshly cut sodium (5 grams) was added to the flask together with 0.25 milliliters of 15-crown-5-ether. This mixture was allowed to reflux for 3 hours. The mixture was then distilled to yield 72.6 grams of trioxane. The trioxane collected was melted into a clear liquid and 2.4 ml of ethylene oxide (3 weight percent based on trioxane) was added. The molten system was then polymerized using 10 microliters of boron trifluoride etherate. The polymer formed which was collected, washed and stabilized by alkaline hydrolysis. The resultant copolymer exhibited a melt index value of 18 showing a high molecular weight.

EXAMPLE 2

As a comparative example, 225 g of commercial trioxane was placed in a 3-neck flask, flushed with argon and melted. About 11 grams of sodium was added and refluxed for 3 hours. At the conclusion of the reflux period, 171.3 grams of trioxane were distilled into a resin flask and melted. The molten trioxane showed signs of partial polymerization, in that, some solid material remained after melting. Thereafter 6 ml of ethylene oxide (3 weight percent based on trioxane) were added and the system polymerized with 23 microliters of boron trifluoride etherate. No melt index value could be obtained on the polymer since the molecular weight was insufficiently high. The inherent viscosity of the recovered polymer was 0.56.

EXAMPLE 3

Commercial trioxane is refluxed with about 2 wt.% freshly cut sodium and about 1 wt.% polyethylene glycol (Mol.Wt.=400) for 3 hrs. under an argon atmosphere and then distilled into a dry resin flask. Once melted, the trioxane should be polymerizable to high molecular weight with a traditional cationic catalyst, such as $BF_3 \cdot OEt_2$.

EXAMPLE 4

225 g commercial trioxane was refluxed for 4 hours under Ar with 5–6 g of sodium and 3.6 ml of diglyme. Then 205.2 g were distilled off into a dry, jacketed, reaction flask. The trioxane was melted at 70° C. to a perfectly clear liquid and 6.8 ml of 1,3-dioxolane were added to it. The system was polymerized by injection of 28 ml of $BR_3 \cdot OET_2$. The resultant crude copolymer was of high molecular weight exhibiting a melt index of 3.21.

While certain embodiments and details have been shown for the purpose of illustrating this invention, it will be apparent to those skilled in this art that various changes and modifications may be made herein without departing from the spirit or scope of the invention.

I claim:

1. A method for removing impurities from trioxane and acetals having the general formula

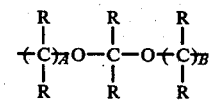

wherein each R is, independently, hydrogen, alkyl groups containing from 1 to 20 carbon atoms and cycloaliphatic or aromatic groups containing from 6 to 20 carbon atoms and A and B are numbers from 1 to about 3, comprising contacting said trioxane or acetal with an alkali metal in the presence of a phase transfer catalyst, refluxing for a time sufficient to purify the acetal, and separating alkali metals and phase transfer catalysts, wherein the phase transfer catalyst is at least one material selected from the group consisting of cryptates, crown ethers, sulfur or nitrogen analogues of crown ethers, and polyethers having the general formula

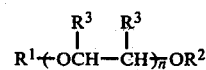

wherein $R^1$, $R^2$, and $R^3$ are, independently, hydrogen or alkyl radicals containing from 1 to 20 carbon atoms, and $n \geq 1$.

2. A method as described in claim 1 wherein the polyether is at least one material selected from the group consisting of polyethylene glycols having the formula $HO\text{-}(CH_2CH_2O)_nH$ where n is from 1 to 14, glyme, diglyme, propylene glycol methyl ether, diethylene glycol, methyl ether, diethylene glycol n-butylether.

3. A method as described in claim 1 wherein the alkali metal is selected from the group consisting of sodium, lithium and potassium.

4. A method as described in claim 3 wherein the acetal is separated from alkali metal and phase transfer catalyst by distillation.

5. A method as described in claim 4 wherein the reflux is carried out for a time ranging from about 1 minute to about 10 hours.

6. A method as described in claim 5 wherein the phase transfer catalyst is present at concentrations of from about 0.01 weight percent to about 10 weight percent based upon the weight of trioxane or acetals present.

7. A method as described in claim 6 wherein the phase transfer catalyst is a crown ether selected from the group consisting of 15-crown-5-ether, 12-crown-4 and 18-crown-6.

* * * * *